United States Patent [19]
Bakaitis et al.

[11] Patent Number: 5,093,079
[45] Date of Patent: Mar. 3, 1992

[54] STERILIZATION APPARATUS AND RELATED PROCESS

[76] Inventors: Teresa L. Bakaitis; Brian S. Bakaitis, both of 1007 Sycamore St., Washington, Pa. 15301

[21] Appl. No.: 317,983

[22] Filed: Mar. 2, 1989

[51] Int. Cl.$^5$ .............................................. A61L 2/00
[52] U.S. Cl. ...................... 422/28; 422/102; 422/103; 134/94; 134/150; 134/166 R; 134/169 R; 15/104.92
[58] Field of Search .................... 422/28, 102, 103; 134/60, 94, 150, 166 R, 169 R, 201; 15/104.92

[56] References Cited

U.S. PATENT DOCUMENTS

| | | | |
|---|---|---|---|
| D. 116,272 | 8/1939 | McKeen | 15/104.92 |
| 2,963,727 | 12/1960 | Roberts | 15/104.92 |
| 4,021,197 | 5/1977 | Brooks | 422/28 |
| 4,551,308 | 11/1985 | Mintz | 422/102 |
| 4,872,235 | 10/1989 | Nielsen | 15/104.92 |

*Primary Examiner*—Robert J. Warden
*Assistant Examiner*—Lyle A. Alexander
*Attorney, Agent, or Firm*—Nixon & Vanderhye

[57] ABSTRACT

Apparatus and method for cleaning and disinfecting medical instruments such as laryngoscope blades are provided. The apparatus includes a container body having exterior walls and interior partitions defining a plurality of chambers defining a soaking area, a scrubbing area, and a pair of rinsing chambers. The container, preferably constructed of plastic, is also formed with integrally hinged covers for the respective chambers. Flexible brush means are provided within the scrubbing chamber. A pair of injection ports are provided in the soaking area of one chamber for receiving a pair of syringes for injecting buffer and activating components of a cleaning and disinfecting solution into the soaking area. A partition extending between the soaking area and the scrubbing area of the one chamber permits the solution to pass freely therebetween. An additional cover is provided to shield the syringes. In a preferred process, a medical instrument is cleaned by the steps of at least partially filling said soaking, scrubbing and rinsing areas with water; injecting the cleaning and disinfecting solution into the soaking area; scrubbing the instrument in said scrubbing area; inserting the instrument into the soaking area for a prescribed period of time; removing said instrument from the soaking area and thereafter inserting it into a first rinsing area; and removing the instrument from the first rinsing area and inserting it in a second rinsing area.

33 Claims, 5 Drawing Sheets 5,093,079

STERILIZATION APPARATUS AND RELATED PROCESS

BACKGROUND AND SUMMARY OF THE INVENTION

This invention relates generally to the sterilization of medical instruments and, more specifically, to the sterilization of the laryngoscope blades.

Presently, there is no standardized procedure for the cleaning and disinfecting of the laryngoscope blades. While certain sterilization procedures have been proposed—see for example, an October, 1974 article in the S.A. Medical Journal entitled "Sterilization of the Laryngoscope Blades" by Jay Carstens—it remains that blades are typically manually scrubbed in a sink, rinsed, and set aside to dry. There are a number of problems associated with this procedure, not the least of which is the fact that soap and water are not effective to kill bacteria. As a result, the unsterile blade, in subsequent use, may introduce harmful pathogens into the trachea and/or pharynx.

In addition, the sink itself and surrounding surfaces may be contaminated, thereby placing other personnel at risk.

The present invention has for its principal object the introduction of a standardized sterilization procedure for laryngoscope blades (or other medical instruments) through the utilization of a simple, easy-to-use, low cost and disposable sterilization unit which, as will be explained below, may be provided in a self-contained kit form. It is contemplated that the apparatus of this invention will be utilized primarily in the numerous and well known health care settings, such as anaesthesia and respiratory care departments, emergency rooms, intensive care units, ambulance units and the like.

In one exemplary embodiment, the sterilization unit includes a substantially upright, plastic container body which is substantially L-shaped in plan and which is formed to provide a plurality of chambers or compartments which open at the top of the container.

A first chamber defines soaking and scrubbing areas and includes a vertically oriented partition to differentiate the soaking area from the scrubbing area. The vertically oriented partition is provided with a plurality of apertures arranged along the height of the container so that cleaning/disinfecting solution is permitted to pass freely between the soaking and scrubbing areas in this first chamber. The scrubbing area of this first chamber is also provided with a plurality of thick but soft cleaning bristles from bottom to top, and protruding inwardly to the center of the scrubbing area. The manner in which the laryngoscope blade is scrubbed in this area will be described in greater detail below.

A second chamber, isolated from the above described first chamber, is utilized in a first rinsing stage following the scrubbing and soaking of the instrument.

A third chamber, adjacent the second chamber, provides a second rinse area and is substantially identical to the second chamber.

Each of the above described chambers is provided with a lid, preferably integrally hinged to the apparatus itself, and including conventional cooperating snap-on/off surfaces which permit the chambers to be closed to thereby prevent the spillage of the liquid therein.

The first chamber is also provided with a pair of injection ports aligned one above the other in a side wall of the unit which partially forms the soaking area of the first chamber. Each port includes a cylindrical projection extending outwardly from a container body side wall and provided with interior threads for receiving a pair of exteriorly threaded, disposable injection syringes. Each port surrounds a resilient rubber or polymer plug secured within the side wall and adapted to be penetrated by an associated syringe.

Each syringe is preferably of unitary plastic construction for ease of disposability as will be explained further hereinbelow. The syringes are employed to introduce into the soaking area of the first chamber, buffer and activating components, respectively, of a cleaning/disinfecting solution. While in this exemplary embodiment, two syringes are described for use in conjunction with the sterilization unit, the dimensions and number of syringes may be varied in accordance with: (1) a type of cleaning/disinfecting solution used and its recommended dilution prior to use; and (2) the volume of water needed to fill the scrub/soak areas of the first chamber. In any event, it is intended that each syringe be prefilled with the correct amount of one of the cleaning/disinfecting solution buffer or activating components in accordance with the solution requirements and the particular sterilization procedure. This arrangement is desirable in that a longer shelf life is provided since, once activated, many solutions are effective for relatively short periods of time, e.g., thirty days.

Each syringe is formed with a barrel portion and an injection needle portion. The latter is designed to receive a resilient plastic bellows or accordion-type cap, which protects users from the sharp needle point. In addition, the cap is designed to remain on the needle and to compress when the syringe is fully screwed into the injection port and to be punctured by the syringe needle. With continuation of the screwing action, the needle will thereafter also penetrate the resilient plug inserted with the side wall of the chamber. It will be appreciated that the compressed cap acts as a secondary seal around the plug to further insure against leakage. It will be further understood that the cleaning/disinfecting solution may then be directly injected into the soaking area of the first chamber, and that the solution will be free to pass between the soaking area and scrubbing area via the apertures provided in the partition wall separating these areas of the first chamber.

It is a further feature of this invention that each of the three above described chambers may be prefilled with correct amounts of sterile or non-sterile water if so desired. Thus, when the cleaning/disinfecting solution is injected into the soak/scrub areas of the first chamber, it will freely mix with the water already present therein.

It will be appreciated, of course, that in the event a cleaning/disinfecting solution is utilized which does not require activation via mixing of separate components, that the injection ports and syringes may be omitted from the container body.

In the exemplary embodiment described above, prefilled syringes are initially screwed into the injection ports so that the bellows cap is closely adjacent but not in engagement with the injection plug in the side wall. In this way, the syringes will be held in a stable position during shipping. The syringes may be further protected during shipping and handling by a removable snap-on/off plastic cover which may be attached directly to exterior walls of the container body so as to completely enclose the syringes.

Just below this removable cover, three reinforcing plates project outwardly away from the container to a point just beyond the lateral extent of the syringes. The combination of the container walls, removable cover and reinforcing plates provide good protection for the syringe and also impart a substantially rectangular, volumetric outline for the container which provides stability and which facilitates packaging and shipping.

It is another feature of this invention that the sterilization unit is adapted to be supported by a bracket which may be attached to a wall, pole, or other mounting surface.

In another aspect of the invention, a larger disposal container is provided which is capable of holding up to six (or more) of the above described sterilization units. Since the individual sterilization units, syringes, and outer disposable containers are all preferably constructed of plastic and/or rubber materials, the disposal container, filled with six "dirty" sterilization units, can be easily disposed of by, for example, incineration, without risk of contamination.

The following preferred procedure is utilized to clean and disinfect a laryngoscope blade in accordance with one exemplary embodiment of the invention. Upon receipt of the sterilization unit, which is intended for single use, or single patient use, the user will prefill the first, second and third compartments with the correct amount of sterile or non-sterile water if this has not already been done. The buffer and activating components of the disinfecting solution are then injected into the scrub/soak area of the first chamber to freely mix with the sterile water therein and to activate the solution. The laryngoscope blade (or other medical instrument) is then inserted into the scrubbing area of the first chamber and thereafter reciprocated in an upward and downward motion while rotating the instrument through the brush bristles to remove all debris and/or tissue from the blade. Thereafter, the laryngoscope blade is removed from the scrubbing area and placed in the soaking area of the first chamber. In this regard, a slot found near the handle of all conventional laryngoscope blades slips easily onto a lip surrounding the open end of any of the chambers so that the blade may hang from the upper edge of the unit while the blade portion is immersed in the solution or sterile water. Once the correct soak time has expired, the blade is removed and thereafter placed immediately into the second chamber in a first rinsing stage. Specifically, the laryngoscope blade is dipped into the first of the two rinsing chambers to remove the majority of the cleaning/disinfecting solution. The blade is then immediately dipped into the third chamber in a second rinsing stage. It is in this second rinsing stage that any diluted cleaning/disinfecting solution remaining on the blade will be removed. The blade is thereafter removed from the third chamber and set aside for drying.

It will be appreciated that the overall dimensions of the sterilization unit and the various chambers are subject to change (including the addition of more than two rinse chambers), depending upon which type of cleaning/disinfecting solution is used, the amount required to insure effective sterilization, and the type of instrument being cleaned. In addition, one or both of the above described syringes may be altered in size or eliminated altogether, depending on the type of cleaning/disinfecting solution used.

It will also be appreciated that the above described sterilization apparatus may also be used for medical scissors, hemostats, and the like. In addition, utilizing the same concept and by slightly altering the dimensions and shape of the container, the apparatus may be custom designed for use with different medical instruments, such as gynecological and dental instruments.

Additional objects and advantages of the invention will become apparent from the detailed description of the drawings which follows.

DETAILED DESCRIPTION OF THE DRAWINGS

Figure 1:
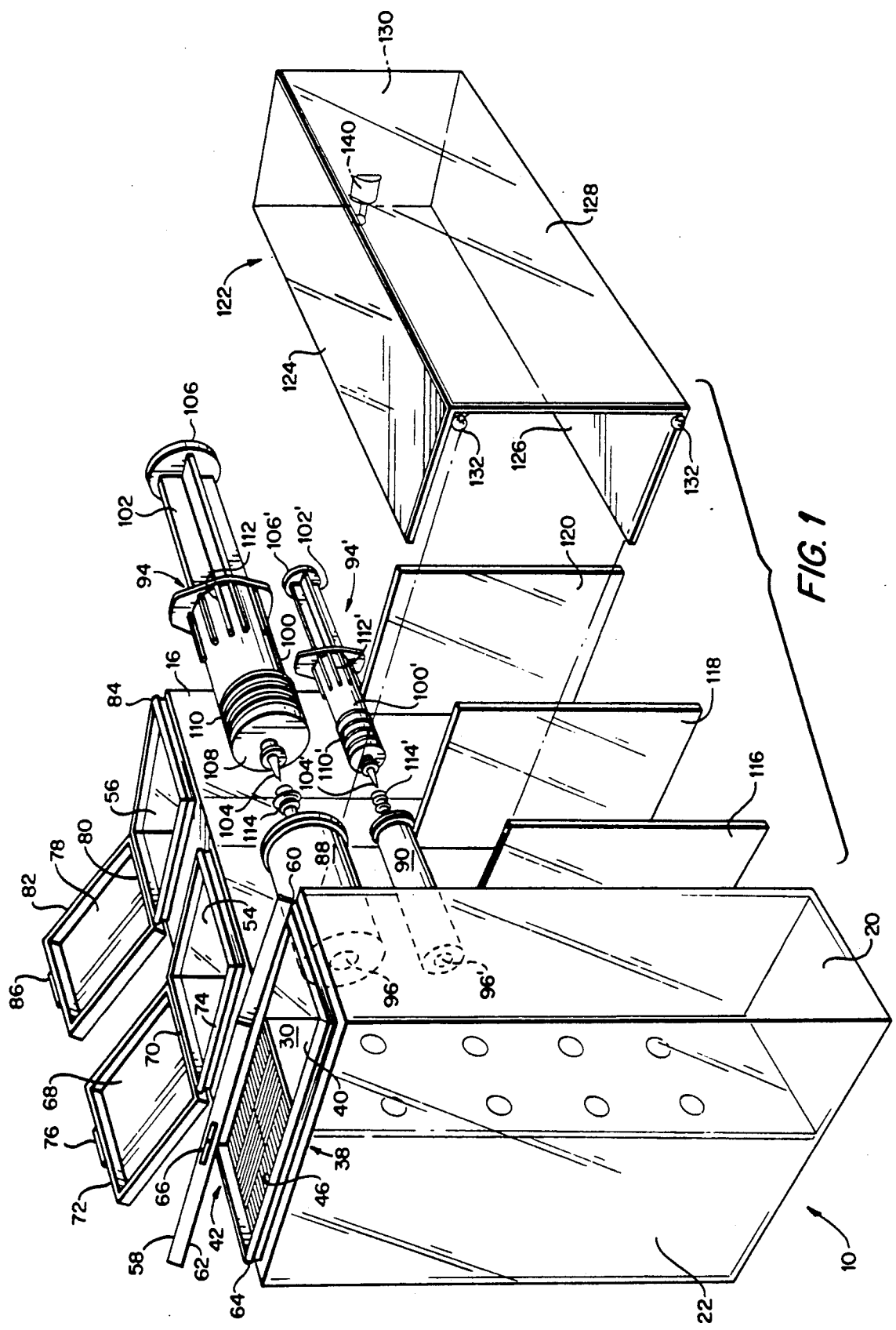
FIG. 1 is a perspective view in exploded form illustrating the components of a sterilization unit in accordance with one exemplary embodiment of the invention.
Figure 2:
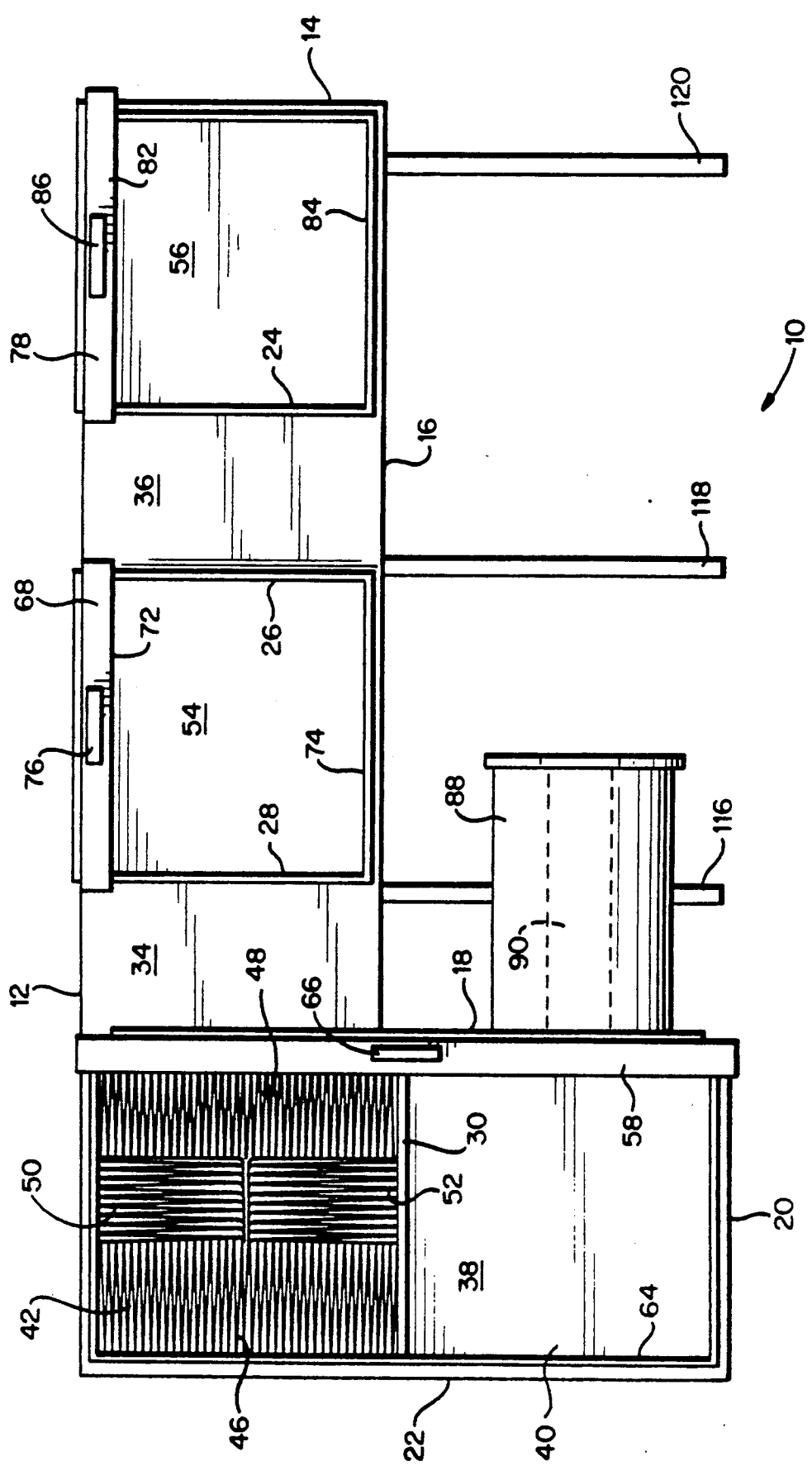
FIG. 2 is a plan view of the container body portion of the apparatus shown in FIG. 1.
Figure 3:
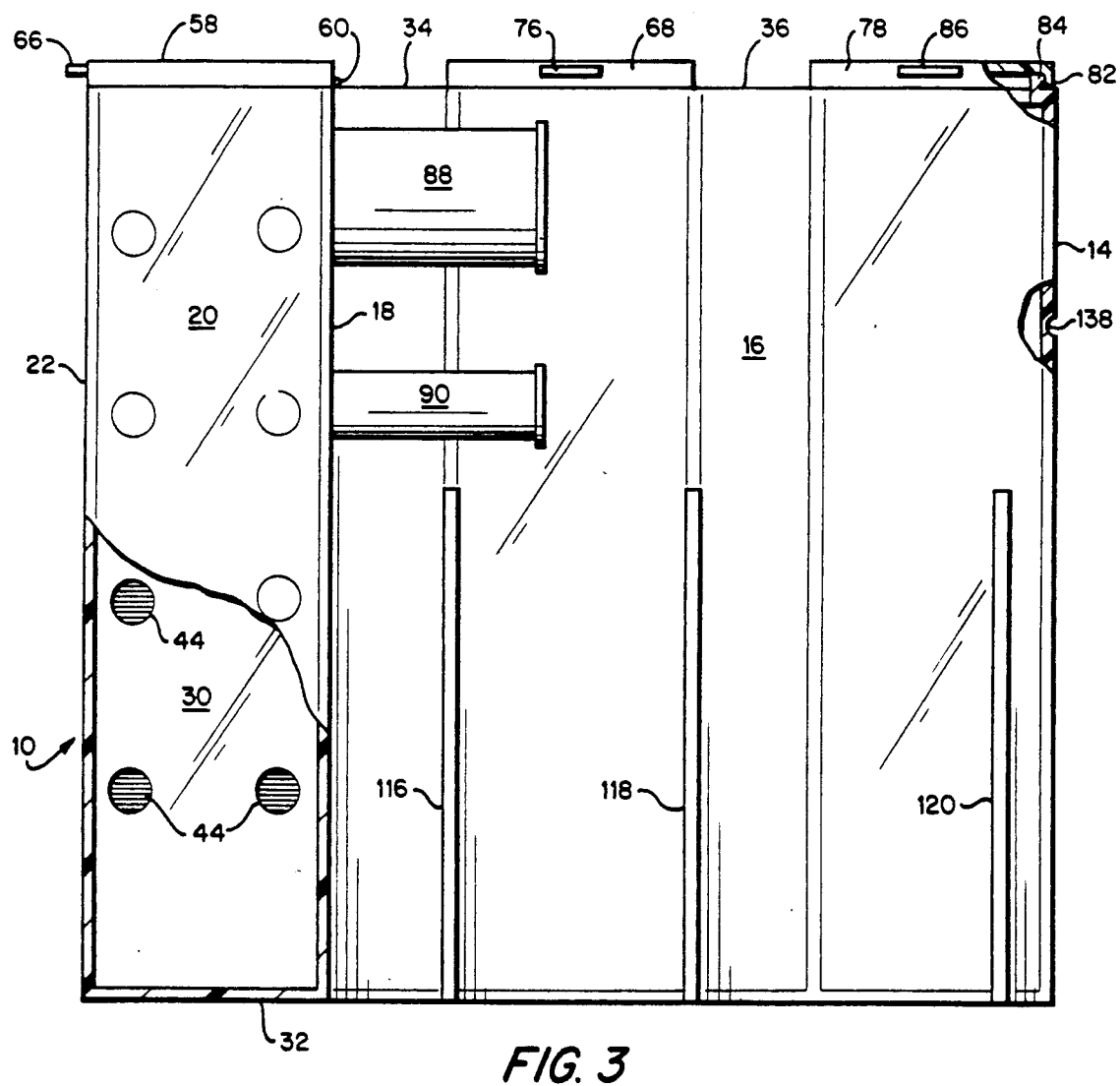
FIG. 3 is a front view of the container body portion shown in FIG. 2, partially broken away to show an interior partition in the container body and other details.

Referring now primarily to FIGS. 1–3, a sterilization unit in accordance with a first exemplary embodiment of the invention includes a container body 10 formed by a back wall 12, a first sidewall 14, a first front wall 16, a second sidewall 18, a second front wall 20 and a third sidewall 22 (which extends between front wall 20 and back wall 12). The walls, all of which are substantially vertically oriented, are arranged to form, in plan, a container body which is essentially L-shaped, with the L rotated clockwise 90°.

Internal partitions 24, 26, 28 and 30, as well as a portion of the sidewall 18 divide the container body into a plurality of chambers, as will be described further hereinbelow. A bottom wall 32 and upper web portions 34, 36 complete the basic structure of the container body 10.

A first interior chamber 38 is formed by sidewalls 18 and 22, front wall 20 and a portion of back wall 12. This chamber is subdivided by the interior partition 30 into a soaking area 40 and a scrubbing area 42. Cleaning/disinfecting solution, or example, of the glutaraldehyde type, such as Sporicidin ®, is free to pass between the soaking and scrubbing areas 40, 42, respectively, by reason of two vertically arranged rows of apertures 44 formed in the interior partition 30, as best seen in FIG. 3. These apertures are preferably ⅛" diameter holes, although it will be appreciated that the number, size and pattern thereof may vary within the scope of this invention.

A plurality of bristle brush elements 46, 48, 50 and 52, (preferable 1/32" diameter, soft plastic bristles) are arranged within the scrubbing area 42, preferably extending from top to bottom of the chamber. The brush elements are arranged to essentially fill all of the free space within the scrubbing area, while permitting a laryngoscope blade to be reciprocated into and out of the area as will be explained further below.

A second chamber 54, utilized in a first rinsing stage, is formed by interior partitions 26, 28 and portions of back wall 12 and front wall 16.

A similar third chamber 56, utilized in a second rinsing stage, is formed by interior partition 24, sidewall 14 and portions of back wall 12 and front wall 16.

The chambers 38, 54 and 56 are laterally separated by a distance corresponding to the lateral extent of webs 34, 36. In order to conserve material and reduce costs, the areas directly beneath webs 34, 36 are hollow, and open at the bottom wall 32.

Each chamber is closed at its lower end by bottom wall 32, and is open at its upper end. Each chamber is provided at its upper open end with a lid movable between open and closed positions. The upper, open end of chamber 38 is provided with a lid 58 which is integrally attached to the upper edge of sidewall 18 by an integral hinge 60. The remaining three edges of the lid 58 are provided with a peripheral lip 62 which snaps over a complimentary flange or lip 64 formed about the upper edges of the corresponding chamber sidewalls. A tab 66 is provided on the lid 58 opposite the hinge 60 to assist in opening and closing the lid 58.

Similarly, the upper, open end of chamber 54 is provided with a lid 68 integrally attached to an upper edge portion of back wall 12 by an integral hinge 70. The remaining three edges of the lid 68 are provided with a peripheral lip 72 which snaps over a complimentary flange or lip 74 formed about the upper edges of the corresponding chamber sidewalls. A tab 76 is provided on the lid to assist in opening and closing the lid 68.

The upper, open end of chamber 56 is likewise provided with a substantially identical lid 78 integrally attached to another upper edge portion of back wall 12 by an integral hinge 80. The remaining three edges of the lid 78 are provided with a peripheral lip 82 which snaps over a complimentary flange or lip 84 formed about the upper edges of the corresponding chamber walls. A tab 86 is provided on the lid to assist in opening and closing movements of the lid 78.

The lids for each of the chambers are effective to prevent spillage before and after an instrument cleaning process.

A pair of injection ports 88, 90 are provided in the sidewall 18 for introducing buffer and activating components of the cleaning/disinfecting solution into the chamber 38. Specifically, a first, relatively larger port 88 projects outwardly from sidewall 18 substantially parallel to the front wall 16. The port is substantially cylindrical in shape and is provided with interior screw threads 92 (FIGS. 4 and 5) for threadably receiving a first injection syringe 94. The port 88 concentrically surrounds a self-sealing injection plug 96 which is secured (by adhesive or other suitable means) within an aperture in the sidewall 18. The plug is preferably formed of rubber or other resilient polymeric material and is formed with a thinned area 98 which is easily penetrated by the plastic syringe needle.

The first injection syringe 94 includes a cylindrical barrel 100 and a shaft 102 that has a rubber plunger 103 attached at its forward end. This plunger 103 acts in the manner of a piston within the cylindrical barrel 100 to expel fluid within the syringe through a needle-like discharge port 104 (hereinafter referred to as the needle). The rearward end of the shaft 102 is provided with a flange 106 which serves as a stop, limiting the forward movement of the plunger 103 and shaft 102 within the barrel 100. The cylindrical barrel 100 is closed at its forward end by an end wall 108, in which is secured the plastic needle 104.

The outer barrel element is provided with exterior screw threads 110, for engagement with threads 92 in the port 88. A series of friction ribs 112 may also be provided on the outer barrel member to facilitate rotating or otherwise handling the syringe.

Figure 4:
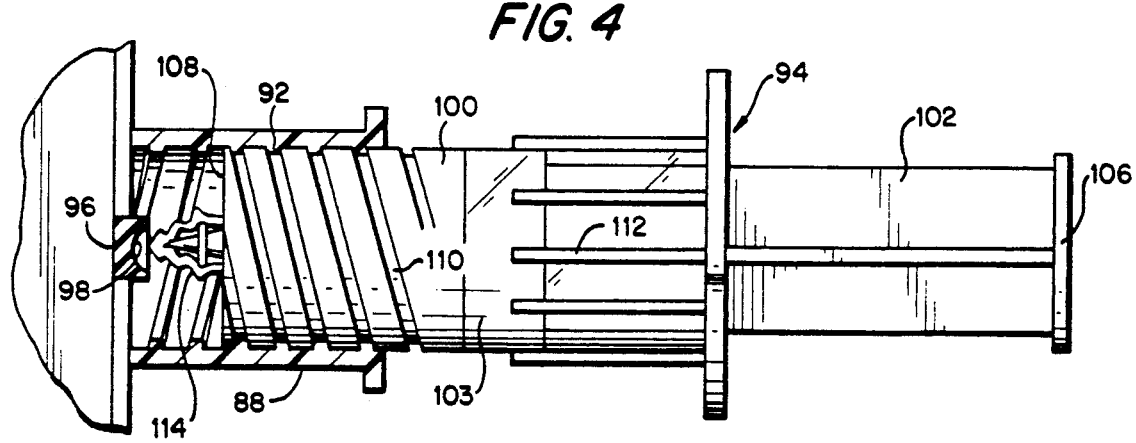
FIG. 4 is a partial section of an injection port and associated syringe in a first inoperative or storage position.
Figure 5:
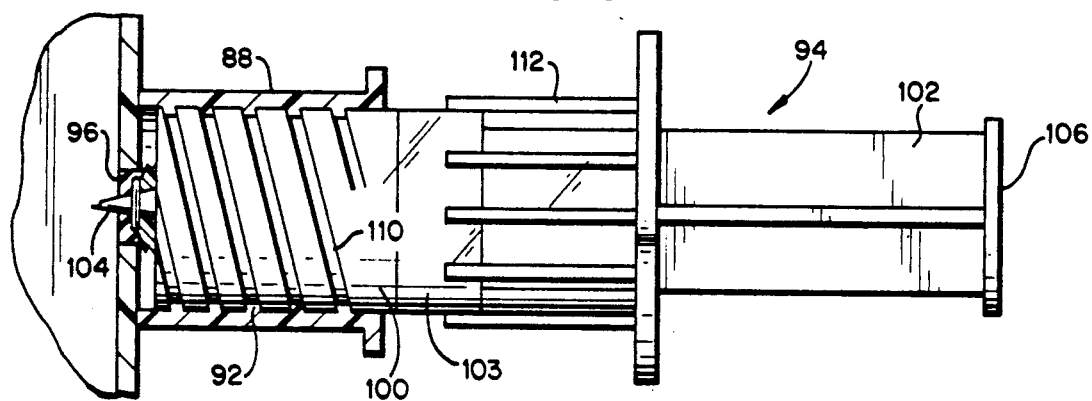
FIG. 5 is a partial section as shown in FIG. 4 but with the syringe in a fully engaged solution injection position.

As best seen in FIGS. 1, 4 and 5, a compressible bellows type cover or cap 114 may be placed over the needle 104 to protect the user (and others) from the sharp, needle point. With reference to FIGS. 4 and 5, it will be seen that the cap 114 is designed to remain on the syringe during assembly and use. Thus, as the syringe 94 is screwed into the port 88, the sharp needle point will penetrate the cap 114 as well as the sealing plug 96 (in the thinned area 98), with the cap axially compressed in the manner illustrated in FIG. 5. As a result, the user is at no time exposed to the needle point of the syringe. At the same time, the cap 114 serves as a secondary seal (along with the plug 96) to prevent escape of solution from the unit.

A second injection syringe 94' is provided directly below the first injection syringe 94 for threaded engagement with the injection port 90. It will be appreciated that this port surrounds a second injection plug 96' (shown in phantom in FIG. 1). In a preferred arrangement, the syringe 94' is substantially identical to syringe 94 with the exception of a smaller barrel diameter. Because of this substantial identity, the same reference numerals, with a prime designation added, are used to denote the various components of syringe 94'.

During shipping and/or storage, the syringes 94, 94' will be threadably received within the injection ports 88, 90, respectively, but in an inoperative or non-injection position, i.e., the syringe needles 104, 104' will lie adjacent the injection plugs 96, 96' but not in engagement therewith. In use, the syringes will be screwed further into the injection ports to thereby penetrate the caps 114, 114' and plugs 96, 96', followed by injection of the cleaning/disinfecting solution components into the soaking area 40 of the first chamber 38.

Directly beneath the syringes 94, 94' are a plurality of vertically arranged, laterally spaced plates 116, 118 and 120 which extend outwardly from the front wall 16 to approximately the forward extent of sidewall 18. These plates serve to reinforce the unit and to protect the syringes 94, 94' during shipping, etc. and further facilitate packaging by contributing to an overall, rectangular volumetric shape of the unit.

As a further measure of protection for the syringes 94, 94', and to further facilitate the packaging of the unit, a substantially C-shaped syringe cover 122 is attachable at the juncture of sidewall 18 and front wall 20, and at the juncture of sidewall 14 and front wall 16, above the plates 116, 118 and 120. Specifically, the cover includes a top wall 124, a bottom wall 126, a front wall 128, and a single sidewall 130, as best seen in FIG. 1.

Figure 6:
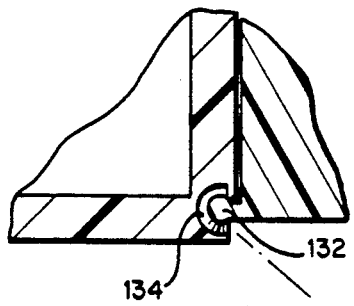
FIGS. 6 and 7 are detailed sections illustrating the manner in which a syringe cover may be applied to the container body.
Figure 7:
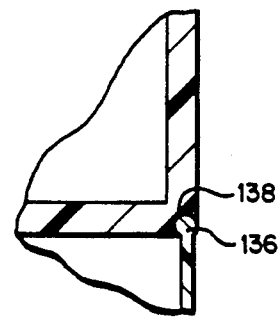

Attachment of the cover to the main housing may be accomplished by any suitable means, so long as easy but secure attachment/removal is provided. In the exemplary embodiment shown in the drawings, and with specific reference to FIGS. 1, 6 and 7, it will be seen that one more projections 132 may be provided along one edge of wall 128 at upper and lower ends thereof. One or more complimentary grooves 134 may also be provided along the corner edge of walls 18 and 20, just above injection port 88, and just below injection port 90. At the same time, a tongue and groove connection may be provided intermediate the upper and lower end of the rearward edge of cover sidewall 130, and at a corresponding location at the juncture of container body walls 14 and 16. The tongue 136 and groove 138 are best seen in FIG. 7. A depressed or recessed region 140 (shown in phantom in FIG. 1) may be provided above the tongue portion 136 for engagement by a user's finger. It will be appreciated that projections 132 may be inserted within grooves 134, and the cover then pivoted inwardly to a fully engaged position, with tongue 136 being snapped into the groove 138. To remove the cover, the user exerts pressure in region 140 to thereby release the tongue 136 from groove 138, permitting an outward pivoting movement until projections 132 may be slidably removed from the grooves 134. It will be understood, of course, that any other suitable means may be employed for removably attaching the cover 122 to the housing 10.

Figure 8:
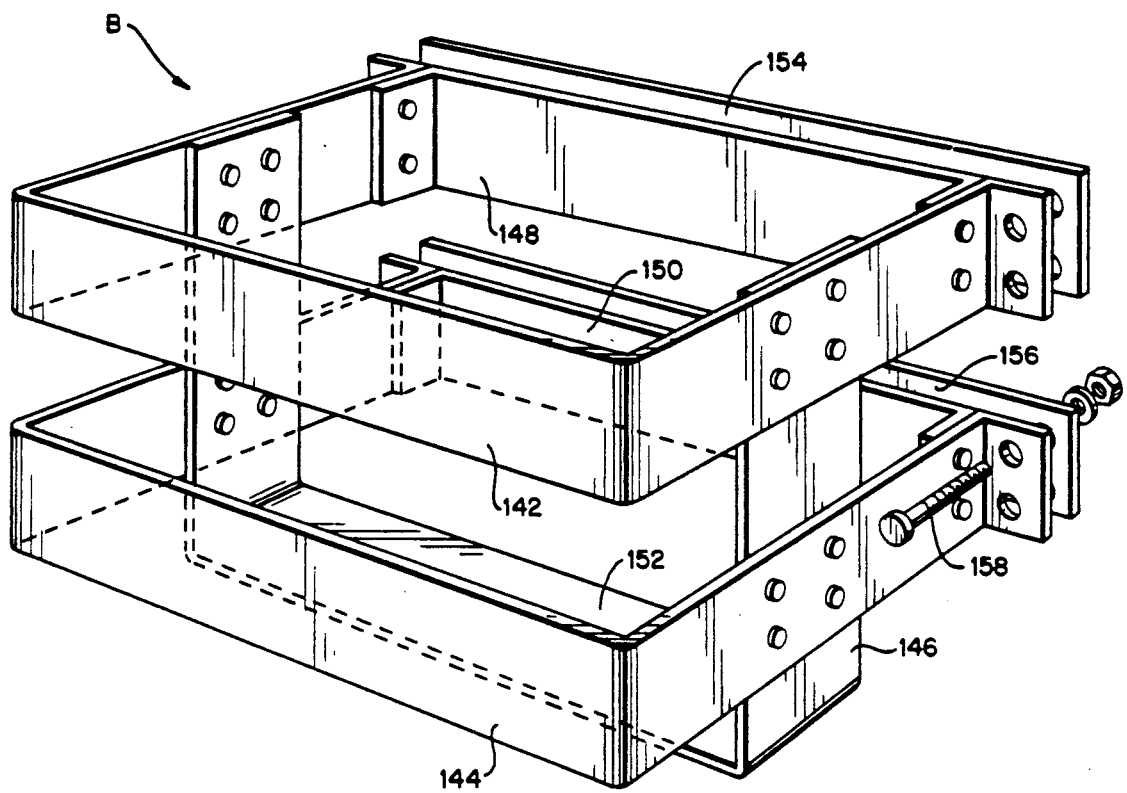
FIG. 8 is a perspective view of a bracket assembly suitable for use with the invention.
Figure 9:
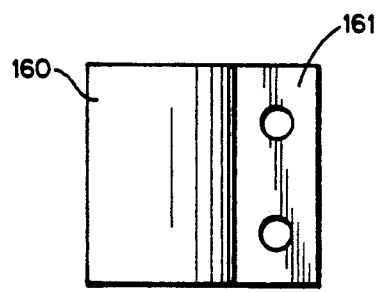
FIGS. 9 and 10 are front and plan views, respectively, of a bracket element suitable for mounting the sterilization unit to a post or pole.
Figure 10:
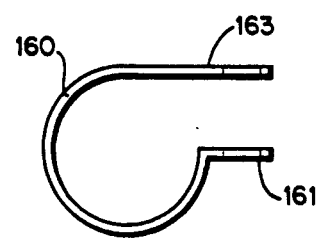

With reference now to FIGS. 8 through 10, one exemplary embodiment of a suitable bracket for wall or post mounting the container body 10 is illustrated. The bracket B comprises a substantially open framework including upper and lower, substantially horizontally oriented U-shaped members 142, 144, and a substantially vertically oriented U-shaped member 146. Rearward straps 148, 150, respectively, extend across the otherwise open ends of members 142, 144 to form a closed rectangular bracket structure. As may be appreciated from FIGURE 8, the unit 10 may be inserted within the bracket, with bottom wall 32 supported on the horizontal leg 152 of the member 146. Additional mounting straps 154, 156 may be provided to facilitate column mounting of the unit. In addition, bracket B can be mounted in either flush or spaced relationship to the wall, using screws 158 in a conventional manner.

In an alternative arrangement, a circular bracket 160 may be fastened to the bracket at the rearward straps 148 or 150, utilizing the mounting flanges 161, 163 of the bracket 160 and suitable fasteners. The circular bracket, in turn, may be mounted for vertically adjustable movement on a pole or post (not shown).

Figure 11:
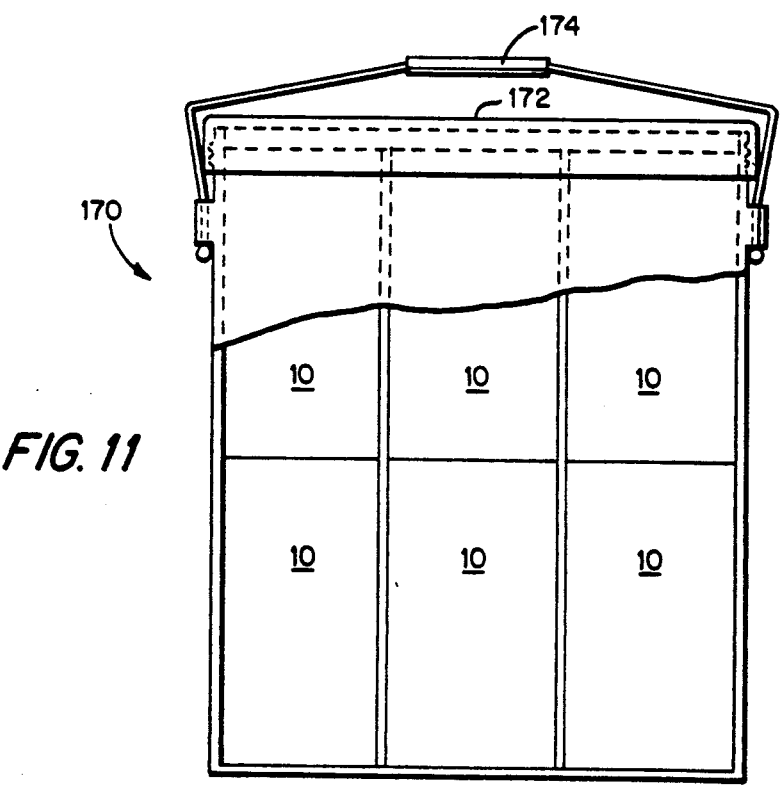
FIG. 11 is a front view of a disposal container for use with the invention, partially broken away to illustrate a plurality of sterilization units stored therein.

In another aspect of the present invention, a plastic disposal container 170 (FIG. 11) is provided which is substantially rectangular in plan, and which has a removable lid 172 and carrying handle 174. The container, lid and handle may be of otherwise conventional construction, and is preferably formed of a plastic material. In accordance with this invention, the container is sized to receive six of the sterilization units 10 in two layers of three each as shown in FIG. 11, although other configurations may be employed. This container 170 also aids in the protective shipping and storage of the units 10.

In the preferred embodiment of the invention, the entire unit 10, including bristle brushes 46, 48, 50 and 52, and also including all elements of syringes 94 and 94' are constructed of a suitable plastic material. The selected plastic must, of course, be inert with respect to the cleaning/disinfectant solution. As already noted, the container 170, its lid 172 and handle 174 are also plastic. In this way, the container and six used units may be easily disposed of by incineration with minimal handling, and thereby minimal risk of contamination.

In a preferred process, utilizing the above described sterilization unit, for sterilization of a medical instrument such as a laryngoscope blade, the following steps are performed. After providing a container body 10 as described hereinabove, the various chambers 38, 54 and 56 are at least partially filled with sterile or non-sterile water (if not prefilled). Thereafter, cleaning and disinfecting solution components, stored within the injection syringes 94, 94' are injected into the soaking area of the container body through the resilient plugs 96, 96' within the injection ports 88, 90, respectively. The instrument is then inserted into the scrubbing area 42, and preferably reciprocated a number of times into and out of the scrubbing area while being rotated, to thereby allow the bristle brush elements 46, 48, 50 and 52 to fully engage and scrub the instrument. The instrument is then inserted into the soaking area 40 for a prescribed period of time. Following the soaking step, the instrument is placed within the first rinsing area 54 to remove the majority of cleaning/disinfecting solution remaining on the blade. Thereafter, the instrument is inserted into the second rinsing stage 56 to remove any remaining cleaning/disinfecting solution. Following the rinsing stages, the instrument is removed from the container body and set aside to dry.

Following the cleaning and disinfecting procedure, the chamber lids are snapped closed and the sterilization unit is placed within the disposal container 170. When a plurality (and in the preferred arrangement 6) of "dirty" units have been placed within the disposal container 170, the entire unit may be disposed of by incineration, thereby minimizing any risk of contamination to the person handling the disposal container.

As previously noted, the sterilization unit of this invention may be provided in a ready to use kit form with the various chambers prefilled with sterile or non-sterile water (and preferably sealed with tamper proof tape or the like) and the syringes prefilled with components of the cleaning/disinfecting solution. Alternatively, the sterilization unit may be shipped with only the syringes prefilled, with the water provided at the point of use.

It will thus be appreciated that the present invention creates a more infection-free environment for health workers; creates a new standard of care regarding infections diseases and cleaning of instruments; and provides an optimum level of safety for all patients as well as health workers.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:
1. Apparatus for cleaning and disinfecting medical instruments comprising:
a container body having exterior walls and substantially vertical interior partitions defining a plurality of chambers, including a first chamber having an instrument soaking area and an instrument scrubbing area, and at least one instrument rinsing chamber, wherein a first substantially vertical partition extends between said soaking and scrubbing areas, said first substantially vertical partition provided with a plurality of apertures for permitting cleaning and disinfecting solution to pass freely therebetween, and wherein instrument scrubbing means are provided in said scrubbing area.

2. Apparatus for cleaning and disinfecting medical instruments according to claim 1 wherein said container body includes at least a second rinsing chamber.

3. Apparatus for cleaning and disinfecting medical instruments according to claim 2 wherein lid means are provided for each of said chambers, said lid means including first and second integrally hinged covers for closing said first and second rinsing chambers, respectively, and a third integrally hinged cover for closing another chamber comprising the soaking and scrubbing areas.

4. Apparatus for cleaning and disinfecting medical instruments according to claim 1 wherein said scrubbing area is provided with brush means extending inwardly from each of four wall surfaces defining said scrubbing area.

5. Apparatus for cleaning and disinfecting medical instruments according to claim 1 wherein said container is constructed of plastic material.

6. Apparatus for cleaning and disinfecting medical instruments comprising:
   a container body having exterior walls and interior substantially vertical partitions defining a plurality of open-top chambers, said plurality of chambers including a first chamber comprising a soaking area and a scrubbing area separated by a substantially vertical internal partition having a plurality of apertures therein, and at least one rinsing chamber isolated from said first chamber and adapted to hold a rinsing fluid, said soaking area including port means for facilitating introduction of medical instrument cleaning and disinfecting solution into said soaking area of said first chamber, wherein said solution is permitted to pass into said scrubbing area from said soaking area through said internal partition, and wherein each of said plurality of chambers has a lid movable between an open position permitting insertion and removal of a medical instrument and a closed position preventing spillage of the cleaning and disinfecting solution and the rinsing fluid.

7. Apparatus for cleaning and disinfecting medical instruments according to claim 6 wherein said port means includes at least one injection port adapted to receive an injection syringe.

8. Apparatus for cleaning and disinfecting medical instruments according to claim 6 wherein said port means includes a pair of injection ports, wherein one of said ports is adapted to receive a first syringe having a first diameter, and the other of said ports is adapted to receive a second syringe having a second diameter smaller than said first diameter.

9. Apparatus for cleaning and disinfecting medical instruments according to claim 7 wherein said injection port comprises a hollow cylindrical projection provided with interior screw threads, said projection surrounding a resilient penetrable plug secured within a wall of said container body.

10. Apparatus for cleaning and disinfecting medical instruments according to claim 8 wherein each said injection port comprises a hollow cylindrical projection provided with interior screw threads, said projection surrounding a resilient penetrable plug secured within a wall of said container body.

11. Apparatus for cleaning and disinfecting medical instruments according to claim g and further including a syringe having a barrel portion and a needle portion, said barrel portion provided with exterior screw threads for engaging said interior screw threads of said cylindrical projection.

12. Apparatus for cleaning and disinfecting medical instruments according to claim 10 and further including a pair of syringes, each having a barrel portion and a needle portion, said barrel portion provided with exterior screw threads for engaging said interior screw threads of one of said cylindrical projections.

13. Apparatus for cleaning and disinfecting medical instruments according to claim 12 and wherein each of said syringes is provided with compressible cap means overlying said needle portion and adapted to be penetrated by said needle portion when said syringe is fully threaded into a respective one of said injection ports.

14. Apparatus for cleaning and disinfecting medical instruments according to claim 8 wherein a removable cover is provided to shield said injection ports and said syringes.

15. Apparatus for cleaning and disinfecting laryngoscope blades comprising:
   a container body having exterior walls and substantially vertical interior partitions defining a plurality of chambers each adapted to receive a laryngoscope blade, a first chamber comprising a soaking area and a scrubbing area, said scrubbing area provided with scrubbing means; a second chamber for a first rinsing stage and a third chamber for a second rinsing stage, said second and third chambers being isolated from said first chamber; one of said interior partitions extending between said soaking area and said scrubbing area in said first chamber having a plurality of apertures therein for permitting cleaning and disinfecting solution to pass freely between said areas;
   injection plug means provided in an exterior wall of said container body for facilitating introduction of cleaning and disinfecting solution into one of said soaking and scrubbing areas of said first chamber;
   injection port means surrounding said plug means;
   at least one injection syringe removably secured within said injection port means; and
   cover means for each of said first, second and third chambers, and for said injection port means including said at least one injection syringe.

16. Apparatus for cleaning and disinfecting medical instruments according to claim 15 wherein said scrubbing means includes brush bristles extending from four wall surfaces defining said scrubbing area inwardly toward a center of said area.

17. Apparatus for cleaning and disinfecting medical instruments according to claim 15 wherein said cover means includes first, second and third integrally hinged, snap-on lids for each of said first, second and third chambers.

18. Apparatus for cleaning and disinfecting medical instruments according to claim 17 wherein said cover means further includes a removable syringe cover for protecting said injection port means and said at least one injection syringe.

19. Apparatus for cleaning and disinfecting medical instruments according to claim 15 wherein said plug means comprises a resilient self sealing member having a thinned area adapted to be penetrated by said syringe.

20. Apparatus for cleaning and disinfecting medical instruments according to claim 15 wherein said at least one syringe includes a needle portion and wherein a compressible cap is provided for covering said needle portion.

21. Apparatus for cleaning and disinfecting medical instruments according to claim 1 and further including a disposal container for carrying a plurality of said container bodies.

22. Apparatus for cleaning and disinfecting medical instruments according to claim 6 and further including a disposal container for carrying a plurality of said container bodies.

23. Apparatus for cleaning and disinfecting medical instruments according to claim 15 and further including a disposal container for carrying a plurality of said container bodies, said disposal container provided with a cover and a handle.

24. Apparatus for cleaning and disinfecting medical instruments according to claim 1 and further including bracket means for supporting said container body on a support surface.

25. Apparatus for cleaning and disinfecting medical instruments according to claim 6 and further including bracket means for supporting said container body on a support surface.

26. Apparatus for cleaning and disinfecting medical instruments according to claim 15 and further including bracket means for supporting said container body on a support surface.

27. A method of cleaning and disinfecting a laryngoscope blade comprising the steps of:
(a) providing a container body having a soaking area, scrubbing area, and at least one rinsing area isolated from said soaking and scrubbing areas, said container body further having injection port means for introducing a cleaning disinfecting solution into one of said soaking and scrubbing areas;
(b) at least partially filling said soaking, scrubbing and rinsing areas with water;
(c) injecting said cleaning and disinfecting solution into one of said soaking and scrubbing areas;
(d) scrubbing said instrument in said scrubbing area;
(e) inserting said laryngoscope blade into said soaking area for a prescribed period of time;
(f) removing said laryngoscope blade from said soaking area and thereafter inserting said laryngoscope blade into said at least one rinsing area; and
(g) removing said laryngoscope blade from said rinsing area and thereafter drying said laryngoscope blade.

28. A method according to claim 27 wherein said container body is provided with at least two rinsing areas and wherein, after step (f), said laryngoscope blade is inserted into a second rinsing area.

29. A method according to claim 27 wherein, after step (g), said container body is placed within a disposal container adapted to hold a plurality of said container bodies.

30. A method according to claim 29 wherein, after a plurality of said container bodies have been placed within said disposal container, said disposal container is incinerated.

31. A method according to claim 27 wherein step (c) is carried out utilizing a pair of injection syringes in cooperation with said injection port means.

32. A method according to claim 31 wherein each syringe contains one component of said cleaning and disinfecting solution.

33. Apparatus for cleaning and disinfecting medical instruments according to claim 6 wherein said scrubbing area includes fixed brush elements for engaging and scrubbing the medical instrument.

* * * * *

UNITED STATES PATENT AND TRADEMARK OFFICE
CERTIFICATE OF CORRECTION

PATENT NO. : 5,093,079
DATED : March 3, 1992
INVENTOR(S) : BAKAITIS et al.

It is certified that error appears in the above-identified patent and that said Letters Patent is hereby corrected as shown below:

In column 10, line 2 of claim 11, "claim g" should read "claim 9".

Signed and Sealed this

First Day of February, 1994

Attest:

BRUCE LEHMAN

Attesting Officer

Commissioner of Patents and Trademarks